(12) United States Patent
Holm

(10) Patent No.: US 9,932,254 B2
(45) Date of Patent: Apr. 3, 2018

(54) METHOD FOR WASTEWATER TREATMENT BY MEANS OF MIXED ALGAE CULTURES THAT SEDIMENT AND DEVICE FOR PERFORMING SAID METHOD

(71) Applicant: Niels Holm, Minden (DE)

(72) Inventor: Niels Holm, Minden (DE)

( * ) Notice: Subject to any disclaimer, the term of this patent is extended or adjusted under 35 U.S.C. 154(b) by 0 days.

(21) Appl. No.: 15/035,081

(22) PCT Filed: Nov. 5, 2014

(86) PCT No.: PCT/DE2014/100392
§ 371 (c)(1),
(2) Date: May 6, 2016

(87) PCT Pub. No.: WO2015/067243
PCT Pub. Date: May 14, 2015

(65) Prior Publication Data
US 2016/0272524 A1    Sep. 22, 2016

(30) Foreign Application Priority Data
Nov. 7, 2013   (DE) .................. 10 2013 112 269

(51) Int. Cl.
*C02F 3/32*     (2006.01)
*A01G 33/00*   (2006.01)
(Continued)

(52) U.S. Cl.
CPC .............. *C02F 3/322* (2013.01); *A01G 33/00* (2013.01); *C02F 1/00* (2013.01); *C12M 21/02* (2013.01);
(Continued)

(58) Field of Classification Search
CPC ...... C02F 3/322; C02F 1/00; C02F 2001/007; A01G 33/00; C12M 21/02; C12M 23/06; C12M 33/22; Y02W 10/33; Y02W 10/37
(Continued)

(56) References Cited

U.S. PATENT DOCUMENTS 4,267,038 A * 5/1981 Thompson .............. C02F 3/302
                                                              210/151
5,880,920 A    3/1999 Fischer et al.
(Continued)

FOREIGN PATENT DOCUMENTS

DE    19611855    8/1997
DE    19721243    11/1998
(Continued)

OTHER PUBLICATIONS

Machine-generated English translation of DE 19752542, translation dated Feb. 28, 2017.*

*Primary Examiner* — Fred Prince
(74) *Attorney, Agent, or Firm* — Diederiks & Whitelaw, PLC

(57) ABSTRACT

The invention relates to a method for treating wastewater by means of photosynthetically active algae that form a sediment in the resting state, comprising the following steps: a) supplying wastewater to photosynthetically active algae that form a sediment in the resting state, b) conveying the wastewater supplied to the algae against gravity from a lower level to a higher level while simultaneously exposing the wastewater mixed with the algae to light, c) introducing the wastewater supplied to the algae from the higher level into the upper region of a sedimentation tank, d) allowing the algae to sediment in the sedimentation tank, and e) removing the wastewater freed of the algae by sedimentation as treated wastewater.

14 Claims, 2 Drawing Sheets

(51) Int. Cl.
*C12M 1/00* (2006.01)
*C12M 1/12* (2006.01)
*C12M 1/26* (2006.01)
*C02F 1/00* (2006.01)

(52) U.S. Cl.
CPC ............ *C12M 23/06* (2013.01); *C12M 33/22* (2013.01); *C02F 2001/007* (2013.01); *Y02W 10/33* (2015.05); *Y02W 10/37* (2015.05)

(58) Field of Classification Search
USPC ............ 210/602, 195.3, 197, 252, 259, 903
See application file for complete search history.

(56) References Cited

U.S. PATENT DOCUMENTS

| | | | |
|---|---|---|---|
| 7,172,691 B2 | 2/2007 | Dunlop et al. | |
| 9,040,283 B2 | 5/2015 | Muller-Feuga | |
| 9,382,508 B2 | 7/2016 | Roeboeck et al. | |
| 2002/0034817 A1* | 3/2002 | Henry | A01G 33/00 435/257.1 |
| 2005/0269259 A1* | 12/2005 | Dunlop | C02F 1/30 210/602 |
| 2010/0264094 A1 | 10/2010 | Schwartz et al. | |

FOREIGN PATENT DOCUMENTS

| | | | |
|---|---|---|---|
| DE | 19752542 | | 7/1999 |
| DE | 19752542 A1 | * | 7/1999 |
| EP | 0078033 | | 5/1983 |
| EP | 1972602 | | 9/2008 |
| GB | 2335199 | | 9/1999 |
| GB | 2335199 A | * | 9/1999 |
| WO | 9845405 | | 10/1998 |
| WO | 2012/104667 | | 8/2012 |
| WO | WO2012/104667 A1 | * | 8/2012 |

* cited by examiner

METHOD FOR WASTEWATER TREATMENT BY MEANS OF MIXED ALGAE CULTURES THAT SEDIMENT AND DEVICE FOR PERFORMING SAID METHOD

CROSS REFERENCE TO RELATED APPLICATIONS

This application is the U.S. National Stage of International Application No. PCT/DE2014/100392, filed 5 Nov. 2014 which claims priority from and the benefit of German Patent Application No. 10 2013 112 269.8 filed on 7 Nov. 2013. The entire contents of these applications are incorporated herein by reference.

BACKGROUND OF THE PRESENT INVENTION

The invention pertains to a procedure for the treatment of sewage by means of photosynthetically active algae and to a device for the conduction of the procedure. In particular, the invention pertains to a procedure and a device, which permits sewage treatment with extensive nutrient recycling by biomass production.

The use of algae mass and/or mixed algae cultures in different plant configurations for biomass production and/or sewage treatment, also in combination with biogas plants, is known already; see DE 196 11 885 C1 and DE 197 21 243 C2, for example. The biomass produced by means of this procedure can be processed for food products. Furthermore, diverse products, such as fine chemicals, vitamins, colouring agents, etcetera, can be extracted as well.

Within the framework of sewage treatment, the biomass accruing is usually treated as a residual material to be disposed of, which for example is disposed of by digestion processes, or which can be added as renewable raw materials to the biogas production in biogas plants.

Regardless of the intended use, the algae biomass has to be removed concentrated from the aqueous culture media in the previous culture technologies.

For various reasons, almost all large culture techniques so far are designed to cultivate floating algae; see DE 197 52 542 A1, for example. Algae can be referred to as floating when they neither swim on the surface nor settle under resting conditions. For this reason, they have to be concentrated and harvested by filtration or centrifugation from the aqueous solution in a rather complex process.

Apart from a number of other technological problems to be taken into account during the cultivation of free-floating algae—such as sufficient $CO_2$ supply and/or prevention of an excessive $O_2$ over-saturation as well as the handling of strongly varying light intensities and temperatures in the course of the day and year, especially in case of open systems—the much too expensive harvesting technique continues to be the main reason for the very sparse large-scale use of this technology to date.

Although a process has been described in EP 1 972 602 B1 already, with which freely floating as well as quickly settling algae populations can be bread in a targeted process.

On the one hand, however, this process has the drawback that on account of the open mode of operation under the climatic conditions given in Central and Northern Europe, where in winter the outside temperatures may drop below freezing and/or the daylight intensity in winter can be so low that no or hardly any net photosynthesis production is possible, the process cannot be operated all-year round, in particular also because any counter-measures to be taken, such as artificial illumination an/or heating, are uneconomic.

On the other hand, however, a research project funded by the DBU (ref. No. 25907) has revealed that a selective cultivation of the easy-to-harvest settling algae based on patent EP 1 972 602 B1 is possible only during very short hydraulic residence times of the water phase, otherwise this will lead to freely floating planktic micro-algae even in case of longer hydraulic residence times.

SUMMARY OF THE INVENTION

For this reason, the objective of the invention is to create a process to treat sewage by means of photosynthetically active algae which will lead exclusively to the formation of settling algae, and which will counter the formation of freely floating algae in order to be able to minimise the biomass harvest.

The basic idea of the invention is to use photosynthetically active algae for sewage treatment instead of freely floating algae, which form a sediment in a state of rest. For this purpose quickly settling mixed algae cultures are used in particular.

The use of quickly settling mixed algae cultures means on the other hand that the previously used tubular systems which—as intended in EP 0 078 033 A1, for example—for the cultivation of freely floating algae consist of vertically arranged individual tubes, having neither a connection with each other nor permitting re-pumping between the individual tube, are not suitable for the execution of the invention-related procedure.

For this reason, the invention-related tubular system has a number of horizontally arranged tubes, which are connected with each other by a rising continuous pipe system. The horizontal arrangement permits an ideal light yield from the sun shining on the tubular system, whereby the vertical line permits the transfer to a sedimentation tank on a higher level, in which the quickly settling algae can be harvested by gravity, and in which the clarified water can be separated. In addition, this type of sewage treatment also prevents the development of freely floating algae.

In particular, the horizontally arranged transparent tubes connected ascendingly with each other are rinsed from bottom to top continuously so quickly that the algae population settling at lower speed cannot settle, but is transported in the water phase from bottom to top.

For this reason the circulation speed should be at least 0.1 m/s. There is no basic upper or lower limit to be observed for the length and width of the entire tubular system. However, the diameter of the individual tube should preferably not be outside of a range of DN 20 mm to DN 200 mm, especially not outside a range of DN 40 mm to 160 mm in particular, depending on the density of the algae culture, the light intensity, and the type of sewage to be treated.

The upper run-off is integrally connected with a sedimentation unit, such as a sedimentation tank known from the classic sewage technology or a parallel plate interceptor. A pump is used to continuously take the water from the lower sedimentation areas of the sedimentation tank to recirculate it into the lowest tube. In this internal re-circulation, which is used for harvesting as well as for preventing settlement, the sewage to be treated/grey water/rinse water/process water is fed preferably into the lowest tube. Exactly the same volume then flows from the clarified water outlet channel of the sedimentation tank as clarified and/or used water, and can drained or used otherwise.

In the process, the invention-related process follows the plug flow principle: The sewage added reaches the sedimentation container only after passing through the entire length of the tubes whereby considerable reaction-kinetic advantages are achieved.

Thus, the invention provides a process to clarify sewage by means of photosynthetically active algae producing a sediment in a state of rest with the steps (a) of feeding sewage to photosynthetically active algae producing a sediment in a state of rest, (b) by moving the sewage fed to the algae from a lower level to a higher level against gravity with light exposure to the sewage blended with the algae at the same time, (c) by adding the sewage fed to the algae on a higher level to the upper area of a sedimentation tank, (d) permitting the sedimentation of the algae in the sedimentation container and (e) permitting the removal of the sewage clarified by the sedimentation of the algae as cleared water. The removal of the clarified sewage is carried out mainly by means of the overflow of the sedimentation tank.

Preferably, the process is carried out continuously by repetition of steps (a) to (e), whereby at least one partial volume of the algae sedimented in step (d) is fed to step (a) causing a circulation when passing through the process again. To put it differently, the algae are passed around in circles, whereby the sewage is fed to the algae circulation between the sedimentation tank and the feeding process against gravity.

In particular, the circulation ensures that the volume of the sewage fed to the algae in step (a) corresponds exactly to the volume of the cleaned sewage running off at the same time.

It is advantageous if feeding of sewage in step (a) when passing through the process again is discontinued when an ammonium concentration predetermined is measured on a higher level, upholding the pure recirculation process until the ammonium concentration drops below the predetermined ammonium concentration. In such a way it is ensured that sewage treatment is really carried out efficiently by setting an ideal ratio between algae and sewage.

In order to prevent the algae from settling in the tubular system already and not only in the sedimentation tank, it is intended that the conveying speed in step (b) shall amount to at least 0.1 m/s. In any case, the conveying speed shall be have to be set in such a way that the algae cannot settle in the tubular system.

The equipment for sewage treatment used to carry out the invention-related process correspondingly provides a multitude of horizontally aligned transparent tubes, which are arranged vertically above each other linked with one another continuously by meander-shaped pipe route, and a sedimentation container to separate the photosynthetically active algae forming a sediment in a state of rest, the run-off of clarified sewage and a hopper tip accepting the algae forming a sediment. Thereby, the topmost tube is connected with the upper area of the sedimentation container, feeding sewage mixed with algae to the sedimentation container. The lowest tube in turn is connected to the hopper tip of the sedimentation container through a pump pumping the sedimenting algae into the hopper tip of the sedimentation container whereby one of the lowest tube feeds sewage.

Preferably the sedimentation container provides an outlet passing the algae biomass from the equipment from the hopper tip of the sedimentation container.

In this case, it is especially preferable that a multitude of algae removal points are arranged in various heights of the sedimentation container, which is linked with the pump.

Finally, in keeping with another preferred execution, the equipment is fitted with a sensor to pick up the ammonium content of the sewage fed to the lowest tube arranged in the upper area of the sedimentation container.

The preferred installation site of such a piece of equipment is the south walls of buildings. By installing directly to the outside building walls, a protection against wind and cold is ensured. The sedimentation container is preferably installed on the inside building wall at the height of the highest tube in order to minimise hydraulic losses.

In order to prevent sewage and/or the aqueous medium containing algae from freezing at minus temperatures, a transparent surface of perspex double plates can be fitted in front of the tube wall, for example.

The advantage achieved by the invention is that the outlay for the biomass harvest is low or is completely absent, and in addition a targeted production of mixed algae cultures settled in a state of rest is ensured, in which the occurrence of floating algae is excluded.

BRIEF DESCRIPTION OF THE DRAWINGS

The invention is illustrated by the drawings, especially preferred execution examples are explained in greater detail. The said illustrate:

FIG. (1) A schematic view from the side of an especially preferred execution example in keeping with the invention; and FIG. (2) A schematic view from the side of an especially preferred sedimentation tank, which can be used preferably within the invention-related equipment.

DETAILED DESCRIPTION OF PREFERRED EMBODIMENTS

Figure 1:
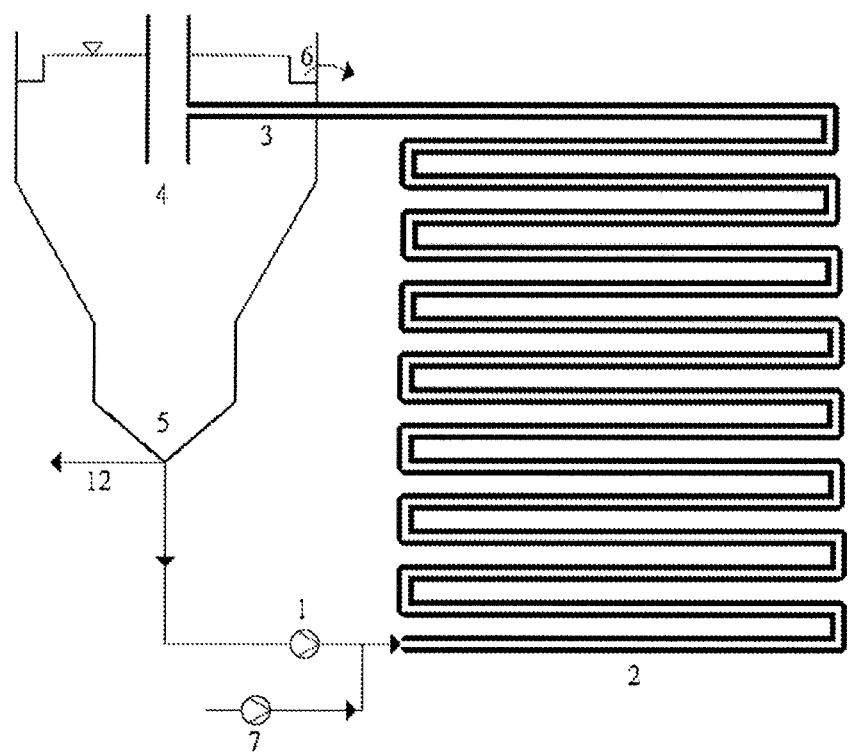
Figure 2:
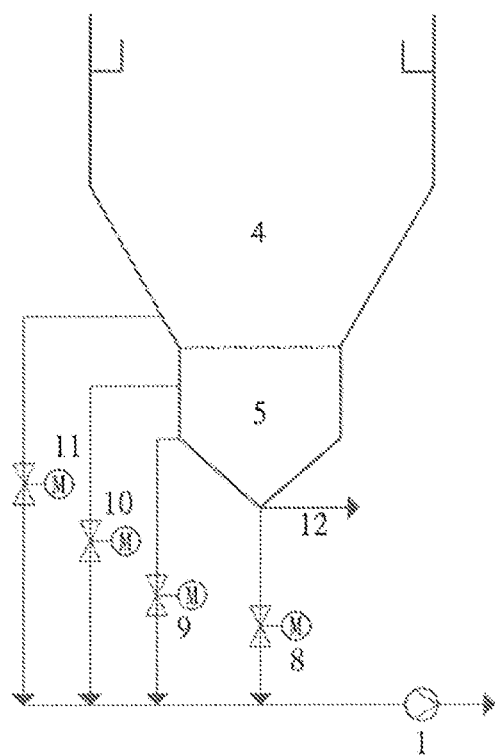

FIG. 1) shows a schematic view from the side of an especially preferred execution example of an equipment in keeping with the invention. At its bottom end, the equipment has been fitted with a pump (1) which causes a preferable circulation of an aqueous culture of easily settling algae in the equipment. In this area, the algae culture is fed with sewage by means of in-feed (7), such as another pump, so that sewage and algae culture can be blended with each other.

This mixture of sewage and algae culture is pumped at least by pump (1) into a multitude of horizontally arranged tubes or rising tube system (2), preferably with a flow speed of at least 0.2 m/s in order to prevent settling of fast settling algae. By this means, the algae together with the sewage is raised against gravity from a lower level to a higher level, whereby a clarifying of the sewage is caused by the biochemical processes based on the mixed algae culture active in the tube system (2).

The topmost tube leads into the inlet area (3) of the sedimentation tank (4). The said is designed as hopper basin, in which the algae settle in the lower hopper tip (5), and the clear water clarified and freed from algae flows off from the upper overflow (6). The in-feed of fresh sewage is ensured by in-feed (7). This results in the fact that at an in-feed of x m³/hour precisely x m³/hour of clarified sewage flows from (6). Without sewage in-feed, the algae culture simply circulates, and is used for biomass production and/or nutrient uptake from the sewage retained in the system. By means of a separate extraction (12), the algae biomass produced can be removed. The hydraulic residence time in the tubular system during the conveying phase should not exceed 48 hours, however, during summer, i.e. during the summer months, and for this reason should be below 48 h because otherwise floating algae would develop in the system.

A special embodiment of the invention relates to the in-feed of the sewage controlled by an on-line measurement of the water quality. For this purpose, an ammonium on-line probe is installed in the in-feed area of the sediment tank (4) shortly before (3), which controls the sewage in-feed as follows: As soon as a freely selected ammonium value is exceeded (such as 0.1 mg/l), the sewage in-feed is interrupted. It is only when the subsequent photosynthesis has led to the underrun of this threshold value that the sewage in-feed is released again.

The decisive parameters of the growth of algae include the algae density in the tubes (in g TS per liter; TS=dry matter). The ideal density value depends on the composition of the mixed algae population and of the light intensity (and of the tube diameter, of course). The lower the light intensity is, the lower the ideal density. This ideal density value is between excessively high density, which reduces the algae yield due to excessive shading, and an insufficient density, at which the yield is reduced due to the photoinhibition. The respectively associated function of density and light intensity can be determined empirically for every mixed algae population. This means that in the course of the day a correspondingly controlled density change would lead to an increase in yield (or improved sewage treatment).

The insensitivity of the mixed algae population against longer anaerobic lingering time, selected for quick settling, as well as the sedimentation tank with a usable storage possibility in the lower hopper area is used for the following special embodiment of the invention:

The empirically determined ideal function of density and light intensity is stored in the programmable logic controller. A TS probe in the tube determines the current density value of the algae population on-line. A light intensity measurement determined the current light intensity on-line. The extraction of the settling mixed algae population from the hopper area of the sedimentation tank (4), as indicated in FIG. (2), controls the different heights in sedimentation tank (4) by means of control valves.

After the highest position of the sun at midday, the light intensity decreases towards evening. Thus, the ideal density decreases more and more. The ideal adjustment is carried out automatically when the light intensity decreases to below the defined threshold value, and the the removal of the algae from the hopper area moves higher and higher and thus is carried out with less algae density. Given these higher removal points, the algae mud settles and is stored temporarily (and harvested potentially) until the light intensity rises next, which in turn will automatically lead to lower removal points with higher algae density.

As shown in FIG. (2), the sedimentation tank (4) is preferably provided with several algae removal points (8), (9), (10) and (11). In case of a very high light intensity, the recirculation in the tubular system is ensured by pump (1) through removal point (8) in the lowest hopper area. As soon as the light intensity drops below the current value belonging to this density, the removal point (9) is opened automatically and the removal point (8) is closed.

Correspondingly the same process will take place at removal points (10) and (11). In case of removal above removal point (8), the algae mud accumulated between the removal points (8) and (9). If and when required, this highly concentrated algae mud can be harvested from removal point (12).

In the process, this harvest can be automated as follows: If the highest position of the sun does not cause the removal point (8) to open with this setting, the quantity is harvested automatically between the removal point (8) and the open removal point open at that point using the removal point (12).

Thus, a partial amount only of the algae settled in step (d) is recirculated preferably depending on the (optical) density of the settled algae.

The invention claimed is:

1. Process to treat sewage by photosynthetically active algae forming a sediment in a state of rest comprising the steps of:
   a. In-feed of sewage to photosynthetically active algae forming a sediment in a state of rest;
   b. Transport against gravity of the sewage fed to the algae from a lower level to a higher level with simultaneous exposure to light of the sewage blended with algae, wherein a conveying speed in step (b) amounts at least to 0.1 m/s;
   c. Redirection of the sewage fed to the algae from the higher level into the upper area of a sedimentation tank;
   d. Sedimenting of the algae in the sedimentation tank; and
   e. Removal of the sewage cleared by the sedimentation of the algae as clarified water.

2. The process of claim 1, wherein the process is carried out continuously by repetition of steps (a) to (e), whereby at least one partial volume of the algae sedimented in step (d) is fed to step (a) causing a circulation when passing through the process again.

3. The process of claim 2, wherein a volume of the sewage fed to the algae in step (a) corresponds exactly to the volume of the cleaned sewage running off at the same time.

4. The process of claim 2, wherein if feeding of sewage in step (a) when passing through the process again is discontinued when an ammonium concentration predetermined is measured on a higher level, upholding the pure recirculation process until the ammonium concentration drops below the predetermined ammonium concentration.

5. The process of claim 1, wherein an hydraulic residence time of the algae during step (b) is no more than 48 h during the summer months.

6. Process to treat sewage by photosynthetically active algae forming a sediment in a state of rest comprising the steps of:
   a. In-feed of sewage to photosynthetically active algae forming a sediment in a state of rest;
   b. Transport against gravity of the sewage fed to the algae from a lower level to a higher level with simultaneous exposure to light of the sewage blended with algae;
   c. Redirection of the sewage fed to the algae from the higher level into the upper area of a sedimentation tank;
   d. Sedimenting of the algae in the sedimentation tank; and
   e. Removal of the sewage cleared by the sedimentation of the algae as clarified water
   wherein the process is carried out continuously by repetition of steps (a) to (e), whereby at least one partial volume of the algae sedimented in step (d) is fed to step (a) causing a circulation when passing through the process again.

7. The process according to claim 6, wherein a volume of the sewage fed to the algae in step (a) corresponds exactly to the volume of the cleaned sewage running off at the same time.

8. The process according to claim 6, wherein if feeding of sewage in step (a) when passing through the process again is discontinued when an ammonium concentration predetermined is measured on a higher level, upholding the pure recirculation process until the ammonium concentration drops below the predetermined ammonium concentration.

9. The process of claim 6, wherein an hydraulic residence time of the algae during step (b) is no more than 48 h during the summer months.

10. Process to treat sewage by photosynthetically active algae forming a sediment in a state of rest comprising the steps of:
   a. In-feed of sewage to photosynthetically active algae forming a sediment in a state of rest;
   b. Transport against gravity of the sewage fed to the algae from a lower level to a higher level with simultaneous exposure to light of the sewage blended with algae, wherein an hydraulic residence time of the algae during step (b) is no more than 48 h during the summer months;
   c. Redirection of the sewage fed to the algae from the higher level into the upper area of a sedimentation tank;
   d. Sedimenting of the algae in the sedimentation tank; and
   e. Removal of the sewage cleared by the sedimentation of the algae as clarified water.

11. Equipment for sewage treatment comprising:
   a multitude of horizontally arranged transparent tubes which arranged vertically above each other and which when linked with one another form a continuous meander shaped pipe route,
   a sedimentation tank used to separate photosynthetically active algae settling in a state of rest from clarified sewage, with a run-off of the clarified sewage, and with a hopper tip accepting the algae forming a sediment, whereby
   a topmost tube is linked with an upper area of the sedimentation tank, feeding sewage mixed with algae to the sedimentation tank,
   a bottommost tube linked to a pump pumping the algae settling in the hopper tip of the sedimentation tank in the bottommost tube is connected with the hopper tip of the sedimentation tank, and
   an in-feed for feeding sewage to the bottommost tube.

12. Equipment according to claim 11, further comprising an outlet passing algae biomass from the equipment from the hopper tip of the sedimentation tank.

13. Equipment according to claim 11, further comprising a multitude of algae removal points arranged at various heights of the sedimentation tank, which are connected to the pump.

14. Equipment according to claim 11, further comprising a sensor to measure an ammonium content, located in the upper area of the sedimentation tank acting on the in-feed of the sewage to the bottommost tube.

* * * * *